(12) United States Patent
Samaritani et al.

(10) Patent No.: US 9,512,215 B2
(45) Date of Patent: Dec. 6, 2016

(54) LIQUID FORMULATIONS OF TUMOR NECROSIS FACTOR-BINDING PROTEINS

(71) Applicant: ARES TRADING S.A., Aubonne (CH)

(72) Inventors: Fabrizio Samaritani, Rome (IT); Alessandra Del Rio, Rome (IT); Rita Agostinetto, Rome (IT)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 14/570,244

(22) Filed: Dec. 15, 2014

(65) Prior Publication Data

US 2015/0098950 A1 Apr. 9, 2015

Related U.S. Application Data

(63) Continuation of application No. 10/547,307, filed as application No. PCT/EP2004/050118 on Feb. 11, 2004, now Pat. No. 8,937,045.

(30) Foreign Application Priority Data

Feb. 28, 2003 (EP) ..................................... 03100505

(51) Int. Cl.
| | |
|---|---|
| *C07K 14/435* | (2006.01) |
| *C07K 16/24* | (2006.01) |
| *A61K 47/02* | (2006.01) |
| *A61K 38/17* | (2006.01) |

(52) U.S. Cl.
CPC ......... *C07K 16/241* (2013.01); *A61K 38/1793* (2013.01); *A61K 47/02* (2013.01); *C07K 2317/94* (2013.01)

(58) Field of Classification Search
CPC .............................. C07K 14/435; A61K 38/17
USPC ...................................................... 514/21.2
See application file for complete search history.

(56) References Cited

U.S. PATENT DOCUMENTS

| | | | |
|---|---|---|---|
| 5,776,895 | A | 7/1998 | Alber et al. |
| 6,225,300 | B1 | 5/2001 | Boe et al. |
| 6,306,820 | B1 | 10/2001 | Bendele et al. |
| 2002/0077294 | A1 | 6/2002 | Kay et al. |
| 2003/0190304 | A1 | 10/2003 | Thompson et al. |

FOREIGN PATENT DOCUMENTS

| | | |
|---|---|---|
| WO | 94/06476 | 3/1994 |
| WO | 97/41895 | 11/1997 |

OTHER PUBLICATIONS

"Rote Liste 2002", Rote Liste Service GmbH, Frankfurt A.M., p. 05 389, 2002. XP002247690.
Gregory B. Stauber: "Human tumor necrosis factor-α receptor", The Journal of Biological Chemistry, vol. 263, No. 35, pp. 19098-19104, 1988.
Hans-Peter Hohmann: "Two different cell types have different major receptors for human tumor necrosis factor (TNFα)", The Journal of Biological Chemistry, vol. 264, No. 25, pp. 14927-14934, 1989.
Manfred Brockhaus: "identification of two types of tumor necrosis factor receptors on human cell lines by monoclonal antibodies", Proc. Natl. Acad. Sci., vol. 87, pp. 3127-3131, Apr. 1990.
Patrick W. Gray: "Cloning of human tumor necrosis factor (TNF) receptor cDNA and expression of recombinant soluble TNF-binding protein", Proc. Natl. Acad. Sci., vol. 87, pp. 7380-7384, Oct. 1990.
Bharat B. Aggarwal: "Characterization of receptors for human tumour necrosis factor and their regulation by γ-interferon", Letters to Nature, Nature, vol. 318, Dec. 1985.
Hartmut Engelmann: "Two tumor necrosis factor-binding proteins purified from human urine", The Journal of Biological Chemistry, vol. 265, No. 3, pp. 1534-1536, 1990.
Hansruedi Loetscher: "Molecular cloning and expression of the human 55 kd tumor necrosis factor receptor", Cell, pp. 351-359, 1990.
Thomas J. Schall: "Molecular cloning and expression of a receptor for human tumor necrosis factor", Cell, vol. 61, pp. 361-370, Apr. 20, 1990.
Craig A. Smith: "A receptor for tumor necrosis factor defines an unusual family of cellular and viral proteins", Science, vol. 248, pp. 1019-1023, May 25, 1990.
Yaron Nophar: "Soluble forms of tumor necrosis factor receptors (TNF-Rs). The cDNA for the type 1 TNF-R, cloned using amino acid sequence data of its soluble form, encodes both the cell surface and a soluble form of the receptor", The FMBO Journal, vol. 9, No. 10, pp. 3269-3278, 1990. XP 002025930.
Manning, (Pharmaceutical Research 6(11), 903-918 1989)).
Wang (International Journal of Pharmaceutrics 185(1), 129-188, 1999).
Schemm (Rocky Mountain Medical Journal 52(9), 791-800, 1955).
Jackson (The American Journal of Emergency Medicine 18(3), 269-270, 2000).
Avi Ashkenazi, et al., "Protection against endotoxic shock by a tumor necrosis factor receptor immunoadhesin", Proc. Natl.Acad. Sci. USA, vol. 88, Dec. 1991, pp. 10535-10539.
Beck, Clinical Pediatrics 46(9), pp. 764-770, 2007.
Morita (Pediatrics 111(2), 227-230, 2003).
Arakawa (Pharmaceutical Research 8(3), 285-291, 1991).

*Primary Examiner* — David Lukton
(74) *Attorney, Agent, or Firm* — Oblon, McClelland, Maier & Neustadt, L.L.P.

(57) ABSTRACT

The invention relates to a stable, pharmaceutically acceptable, aqueous formulation of TNF-binding protein, comprising a TNF-binding protein, a buffer and an isotonicity agent.

14 Claims, 7 Drawing Sheets

Graph 1- Linear regression lines for onercept formul. bulk at 5 mg/ml and 50

PHO= sodium phosphate buffer mg/ml in 10mM phosphate buffer. (Stability data at +40±2°C)

Graph 2- Linear regression lines for onercept formul. bulk at 5 mg/ml and 50 mg/ml in 10mM acetate buffer. (Stability data at +40±2°C)

ACE= sodium acetate buffer

Graph 3- Linear regression lines for onercept formul. bulk at 5 mg/ml and 50 mg/ml in 10mM citrate buffer. (Stability data at +40±2°C)

CITR= sodium citrate buffer

Graph 4-   Linear regression lines for onercept formul. bulk at 5 mg/ml at different ionic strength. (Stability data at +40±2°C)

PHO= sodium posphate buffer

Graph 5- Linear regression lines for onercept formul. bulk at 50 mg/ml at different ionic strength. (Stability data at +40±2°C)

PHO= sodium phosphate buffer

Graph 6-   Linear regression lines for onercept formul. bulk at 5 mg/ml with excipients. (Stability data at +40±2°C)

Graph 7- Linear regression lines for onercept formul. bulk at 50 mg/ml with excipients. (Stability data at +40±2°C)

LIQUID FORMULATIONS OF TUMOR NECROSIS FACTOR-BINDING PROTEINS

This application is a Continuation of U.S. application Ser. No. 10/547,307, filed Oct. 11, 2006, which is the National Stage of PCT/EP04/50118, filed Feb. 11, 2004, which claimed priority to European application no. 03100505.1, filed Feb. 28, 2003; of which all of the disclosures are incorporated herein by reference in their entireties.

FIELD OF THE INVENTION

This invention relates to liquid, stable formulations of TNF-Binding Proteins.

BACKGROUND OF THE INVENTION

Tumor necrosis factor-alpha (TNF-α), a potent cytokine, elicits a broad spectrum of biologic responses, which are mediated by binding to a cell surface receptor. Stauber et al. "Human tumor necrosis factor-alpha receptor: purification by immunoaffinity chromatography and initial characterization" (*J. Biol. Chem.* 263: 19098-19104, 1988) isolated the receptor for human TNF-alpha from a human histiocytic lymphoma cell line. Hohmann et al. "Two different cell types have different major receptors for human tumor necrosis factor (TNF-alpha)" (*J. Biol. Chem.* 264: 14927-14934, 1989) concluded that there are 2 different proteins that serve as major receptors for TNF-alpha, one associated with myeloid cells and one associated with epithelial cells.

Using monoclonal antibodies, Brockhaus et al. "Identification of two types of tumor necrosis factor receptors on human cell lines by monoclonal antibodies" (*Proc. Nat. Acad. Sci.* 87: 3127-3131, 1990) obtained evidence for 2 distinct TNF-binding proteins, both of which bind TNF-alpha and TNF-beta specifically and with high affinity. Gray et al. "Cloning of human tumor necrosis factor (TNF) receptor cDNA and expression of recombinant soluble TNF-binding protein" (*Proc. Nat. Acad. Sci.* 87: 7380-7384, 1990) isolated the cDNA for one of the receptors. They found that it encodes a protein of 455 amino acids that is divided into an extracellular domain of 171 residues and a cytoplasmic domain of 221 residues. Aggarwal et al. "Characterization of receptors for human tumour necrosis factor and their regulation by gamma-interferon" (*Nature* 318: 665-667, 1985) showed that tumor necrosis factors alpha and beta initiate their effects on cell function by binding to common cell surface receptors. The TNFA and TNFB receptors have different sizes and are expressed differentially in different cell lines (see Hohmann et al., 1989; and Engelmann et al. "Two tumor necrosis factor-binding proteins purified from human urine: evidence for immunological cross-reactivity with cell surface tumor necrosis factor receptors." (*J. Biol. Chem.* 265: 1531-1536, 1990)).

TNF-α-R, referred to by some as TNFR55, is the smaller of the 2 receptors. cDNAs for both receptors have been cloned and their nucleic acid sequence determined (see Loetscher et al. "Molecular cloning and expression of the human 55 kd tumor necrosis factor receptor." (*Cell* 61: 351-359, 1990); Nophar et al. "Soluble forms of tumor necrosis factor receptors (TNF-Rs): the cDNA for the type I TNF-R, cloned using amino acid sequence data of its soluble form, encodes both the cell surface and a soluble form of the receptor" (*EMBO J.* 9: 3269-3278, 1990); Schall et al. "Molecular cloning and expression of a receptor for human tumor necrosis factor." (*Cell* 61: 361-370, 1990); Smith et al. "A receptor for tumor necrosis factor defines an unusual family of cellular and viral proteins." (*Science* 248: 1019-1023, 1990).

Proteins are known to undergo several degradative pathways, especially deamidation, aggregation, clipping of the peptide backbone and oxidation. Many of these reactions can be slowed significantly by removal of water from the protein.

However, the development of an aqueous formulation for drug proteins has the advantages of eliminating reconstitution errors, thereby increasing dosing accuracy, as well as simplifying the use of the product clinically, thereby increasing patient compliance. Thus, it is an objective of this invention to provide an aqueous formulation of TNF-binding proteins, which provides acceptable control of degradation products, is stable to vigorous agitation (which induces aggregation), and is resistant to microbial contamination (which allows "multiple use" or "multi-dose" packaging).

DESCRIPTION OF THE INVENTION

Figure 1:
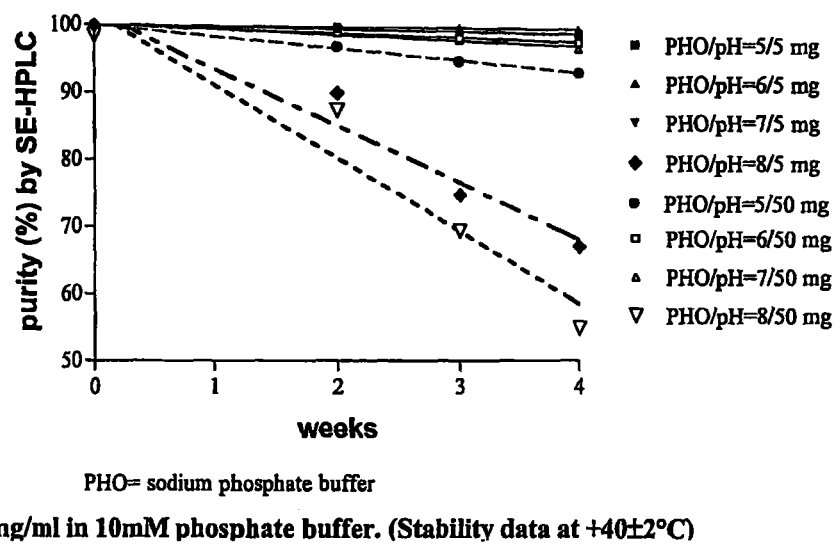
FIG. 1 shows linear regression lines for onercept formulated bulk at 5 mg/ml and 50 mg/ml in 10 mM phosphate buffer (stability data at +40±2° C.).

The main object of the present invention is therefore a stable, pharmaceutically acceptable, aqueous formulation of TNF-binding protein comprising a TNF-binding protein human, a buffer and an isotonicity agent. In one embodiment, the concentration of the buffer is from 5 to 150 mM. In another embodiment, the concentration of the isotonicity agent is from 5 to 50 mM.

Preferably the pH of the solution is kept between 6 and 7 by using a buffer. The buffer can be any pharmaceutically acceptable buffer, which is able to maintain such a pH. Preferably it is phosphate buffer.

The isotonicity agent may be any pharmaceutically acceptable agent, which includes any neutral salt or sugar. For example it can be sodium chloride or mannitol.

A preservative may be included in the formulation to retard microbial growth and thereby allow "multiple use" or "multi-dose" packaging of the TNF-binding protein. Preservatives include phenol, benzyl alcohol, meta-cresol, methyl paraben, propyl paraben, benzalconium chloride, and benzethonium chloride. The preferred preservatives include m-cresol and benzyl alcohol.

The liquid formulations of the invention can also be freeze-dried or lyophilised, if needed.

According to the present invention "TNF-binding proteins" means any protein, which has an affinity for TNF-alpha or TNF-beta and/or a protein, which comprises in full or in part the extra-cellular, soluble fragment of a protein belonging to the TNF receptors family.

Some examples of members of the TNF receptor family are the following:

Tumor Necrosis Factor Receptor 1 (TNFR1), also called Tumor Necrosis Factor Receptor Superfamily, Member 1A (TNFRSF1A), or Tumor Necrosis Factor-alpha Receptor (TNFAR) or TNFR 55-KD or TNFR 60-KD (see description at OMIM*191190 http://www.ncbi.nlm.nih.gov/entrez/query.fcgi?db=OMIM)

Tumor Necrosis Factor Receptor 2 (TNFR2), also called Tumor Necrosis Factor Receptor Subfamily, Member 1B (TNFRSF1B), or Tumor Necrosis Factor-beta Receptor (TNFBR) or TNFR 75-KD or TNFR 80-KD (see description at OMIM*191191);

OX40 Antigen (OX40), also called Tumor Necrosis Factor Receptor Superfamily, Member 4 (TNFRSF4), or Tax-Transcriptionally Activated Glycoprotein 1 Receptor (TXGP1L) or Lymphoid Activation Antigen ACT35 (ACT35) or CD134 (see description at OMIM*600315);

CD40L Receptor (CD40), also called Tumor Necrosis Factor Receptor Superfamily, Member 5 (TNFRSF5) or B-cell surface antigen CD40, or CDw40 or Bp50 (see description at Swiss-Prot Entry No. P25942);

FASL Receptor (FAS), also called Tumor Necrosis Factor Receptor Superfamily, Member 6 (TNFRSF6), or Apoptosis-Mediating Surface Antigen FAS or Apo-1 Antigen or CD95 (see description at Swiss-Prot Entry No. P25445);

Decoy Receptor 3 (DcR3), also called Tumor Necrosis Factor Receptor Superfamily, Member 6B (TNFRSF6B) or Decoy Receptor for FAS Ligand or M68 (see description at Swiss-Prot Entry No. O95407);

CD27 Atnigen (CD27), also called Tumor Necrosis Factor Receptor Superfamily, Member 7 (TNFRSF7) or T-Cell Activation Antigen S152 (S152) (see description at OMIM*602250);

Lymphoid Activation Antigen CD30 (CD 30), also called Tumor Necrosis Factor Receptor Superfamily, Member 8 (TNFRSF8) (see description at OMIM*153243)

Induced By Lymphocyte Activation (ILA), also called Tumor Necrosis Factor Receptor Superfamily, Member 9 (TNFRSF9) or CD137 (see description at OMIM*602250);

Death Receptor 4 (DR4), also called Tumor Necrosis Factor Receptor Superfamily, Member 10A (TNFRSF10A), or TNF-Related Apoptosis-Inducing Ligand Receptor 1 (TRAILR1) or AP02 (see description at OMIM*603611);

Death Receptor 5 (DR5), also called Tumor Necrosis Factor Receptor Superfamily, Member 10B (TNFRSF10B), or TNF-Related Apoptosis-Inducing Ligand Receptor 2 (TRAILR2) or Killer/DR5 or TRICK2 (see description at OMIM*603612);

Decoy Receptor 1 (DCR1), also called Tumor Necrosis Factor Receptor Superfamily, Member 10C (TNFRSF10C), or TNF-Related Apoptosis-Inducing Ligand Receptor 3 (TRAILR3), or TRAIL Receptor Without An Intracellular Domain (TRID) (see description at OMIM*603613);

Decoy Receptor 2 (DCR2), also called Tumor Necrosis Factor Receptor Superfamily, Member 10D (TNFRSF10D) or TNF-Related Apoptosis-Inducing Ligand Receptor 4 (TRAILR4) or TRAIL Receptor With A Truncated Death Domain (TRUNDD) (see description at OMIM*603014);

Receptor Activator of NF-KAPPA-B (RANK), also called Tumor Necrosis Factor Receptor Superfamily, Member 11A (TNFRSF11A), or Osteoclast Differentiation Factor Receptor (ODFR) or PDB2 or TRANCER (see description at OMIM*603499);

Osteoprotegerin (OPG), also called Tumor Necrosis Factor Receptor Superfamily, Member 11B (TNFRSF11B) or Osteoclastogenesis Inhibitory Factor (OCIF) (see description at OMIM*602643);

Death Receptor 3 (DR3), also called Tumor Necrosis Factor Receptor Superfamily, Member 12 (TNFRSF12), or APO3 or Lymphocyte-Associated Receptor of Death (LARD) (see description at OMIM*603366);

Transmembrane Activator And Caml Interactor (TACI), also called Tumor Necrosis Factor Receptor Superfamily, Member 13B (TNFRSF13B) (see description at OMIM*604907);

BAFF Receptor (BAFFR), also called Tumor Necrosis Factor Receptor Superfamily, Member 13C (TNFRSF13C), or B Cell-Activating Factor Receptor (see description at OMIM*606269);

Herpesvirus Entry Mediator (HVEM), also called Tumor Necrosis Factor Receptor Superfamily, Member 14 (TNFRSF14), or Herpesvirus Entry Mediator A (HVEA) or TR2 (see description at OMIM*602746);

Nerve Growth Factor Receptor (NGFR), also called Tumor Necrosis Factor Receptor Superfamily, Member 16 (TNFRSF16) or p75(NTR) (see description at OMIM*162010);

B-Cell Maturation Factor (BCMA), also called Tumor Necrosis Factor Receptor Superfamily, Member 17 (TNFRSF17) or BCM (see description at OMIM*109545);

Glucocorticoid-Induced TNFR-Related Gene (GITR), also called Tumor Necrosis Factor Receptor Superfamily, Member 18 (TNFRSF18), or Activation-Inducible TNFR Family Member (AITR) (see description at OMIM*603905);

TRADE, also called Tumor Necrosis Factor Receptor Superfamily, Member 19 (TNFRSF19), or Toxicity and JNK Inducer or TROY or TAJ (see description at Swiss-Prot Entry No. Q9NS68);

X-linked Ectodyplasin-A2 Receptor (XEDAR), also called EDA-A2 receptor (see description at Swiss-Prot Entry No. Q9HAV5) and DEATH RECEPTOR 6 (DR6), also called Tumor Necrosis Factor Receptor Superfamily, Member 21 (TNFRSF21) (see description at OMIM*605732).

In one embodiment, the TNF-binding protein is TBP-1. In another embodiment, the TNF-binding protein is TBP-2. According to a preferred embodiment of the invention the TNF-binding protein is selected between recombinant h-TBP-1 (recombinant, extracellular, soluble fragment of human TNF Receptor-1, comprising the amino acid sequence corresponding to the 20-180 amino acids fragment of Nophar et al.), whose International Non-proprietry Name (INN) is "onercept", and recombinant h-TBP-2 (recombinant, extracellular, soluble fragment of TNF Receptor-2, comprising the amino acid sequence corresponding to 23-257 of Smith et al.). Most preferably it is recombinant hTBP-1 (r-hTBP-1). For all the other proteins the soluble, extracellular domain is indicated in the corresponding Swiss-Prot entry.

In a different embodiment, the concentration of TNF-binding protein is comprised between 5 and 170 mg/ml.

In one embodiment, the formulation comprises TBP-1, 0.1 M sodium phosphate buffer at pH=6.5 and 0.025 M sodium chloride.

Another embodiment is directed to a process for the preparation of a liquid pharmaceutical formulation, comprising the dilution of the TNF-binding protein with a solution of excipients.

Yet, another embodiment is directed to a presentation form of the liquid pharmaceutical formulation, hermetically sealed in sterile conditions in a contained appropriate for storage prior to use.

In the attempt to find a stable, liquid formulation, the effect of pH/buffer, ionic strength and excipients was evaluated. The description that follows reports on experiments carried out with TBP-1 (onercept).

EXAMPLES

Materials
Onercept drug substance (supplied by Istituto di Ricerca Cesare Serono, Ardea, IT)
Acetonitrile (Merck)
Acetic acid glacial (Merck)
Ammonium sulphate (Merck)
Citric acid (Merck)
D(+)-Glucose monohydrate (Merck)
D (+)-Mannitol (Merck)
Saccharose (Merck)
Sodium azide (Merck)
Sodium chloride (Merck)
Sodium hydroxide (Merck)
Sodium sulphate anhydrous (Merck)
Sodium dihydrogen phosphate monohydrate (Merck)
di-Sodium hydrogen phosphate dihydrate (Merck)
Trifluoroacetic acid (Baker)
Equipment
HPLC systems (Waters)
Calibrated pipettes (Gilson)
Stainless steel holders (Sartorius)
pH meters (mod. 713, Metrohm)
Osmometer (Osmomat 030-D, Gonotec)
Membrane filters 0.45 μm and 0.22 μm (cod. HVLP04700 and GWVP04700, Millipore)
Column TSK gel G2000 SWXL (cod. 08540, TosoHaas)
Column TSKgel Phenyl-5PW Glass 0.8 IDx7.5 cm (cod 08804, TosoHaas)
Primary Packaging Material
Borosylicate type I glass vials (DIN 2R, Nuova Ompi)
Flurotec rubber stoppers (S2F452, D777-1, B2-40, Daikyo Seiko)
Borosilicate Type I glass syringes (HYPAK SCF syringe barrels with fixed needle and needle shield-SCF 1.0 mL long W 7974 grey—Becton Dickinson)
Flurotec stoppers, 1 mL-1 BG B2-40c FLT 4023/50 gr (Daykio)
Bromobutyl stoppers (HYPAK SCF plunger stoppers—BSCF 1.0 mLL 4023/50 grey (Becton Dickinson)
Analytical Tests and Methods
The following analytical tests and methods were used:
pH (potentiometric)
appearance (colour, clarity/opalescence, particles) (visual inspection)
purity and assay by SE-HPLC (working instruction TF 08/01)
purity by HI-HPLC (working instruction TF 09/01)
osmolality (cryoscopic measurement), at time zero only
bioassay First of all, the effect of pH/buffer, ionic strength and excipients was evaluated. The compatibility with stoppers (coated and uncoated) was evaluated as well. Once selected the best conditions, the following three strengths were investigated in pre-filled syringes:
10 mg/mL
50 mg/mL
60 mg/mL A stability study was performed up to 3 months after storage at +5±3° C.; +25±2° C. and +40±2° C. and the following tests were executed:
pH
appearance (colour, clarity/opalescence, particles; by visual inspection)
assay (by SE-HPLC)
purity (by SE-HPLC)
purity (by HI-HPLC)
osmolality (at time zero only)
bioassay
pH Effect In order to test the effect of pH/buffer, solutions of onercept at 5 mg/ml and 50 mg/ml were prepared by dilution of the drug substance in the following 10 mM buffers at different pH:

1. sodium acetate at pH 4, 5 and 6
2. sodium citrate at pH 4, 5, 6 and 7
3. sodium phosphate at pH 5, 6, 7 and 8

The solutions (about 20 ml/batch) were filled into 3 ml glass vials (1 ml filling volume), capped, stoppered and stored at +5±3° C., +25±2° C. and +40±2° C. to be analysed weekly up to 1 month.

Figure 2:
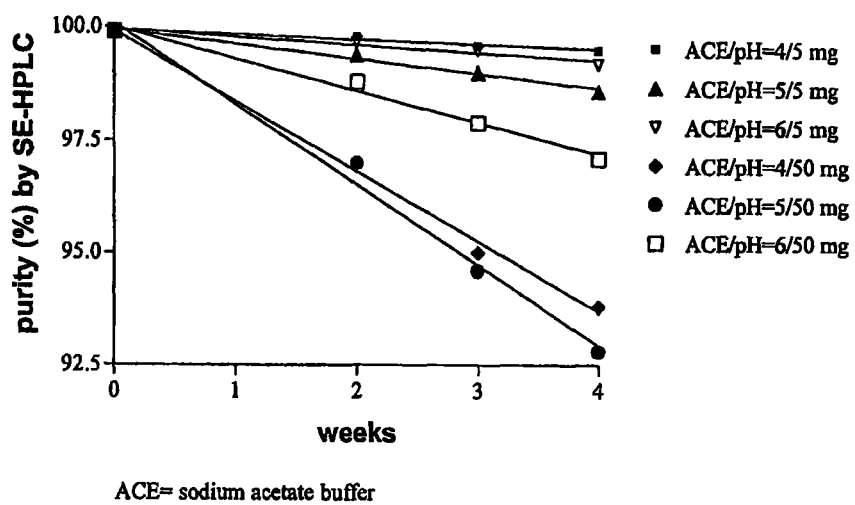
FIG. 2 shows linear regression lines for onercept formulated bulk at 5 mg/ml and 50 mg/ml in 10 mM acetate buffer (stability data at +40±2° C.).
Figure 3:
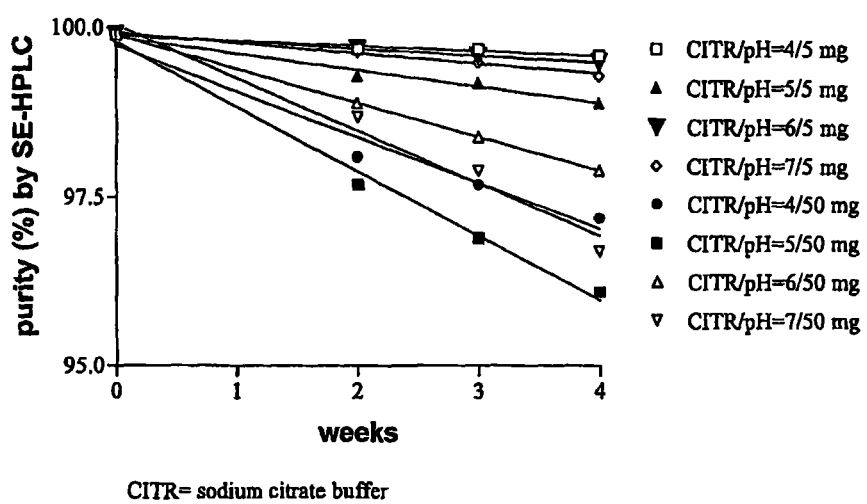
FIG. 3 shows linear regression lines for onercept formulated bulk at 5 mg/ml and 50 mg/ml in 10 mM citrate buffer (stability data at +40±2° C.).

Results were as shown by the Graphs of FIGS. 1, 2 and 3 and by Table 1:

TABLE 1

Onercept formulated bulk at 5 mg/ml and 50 mg/ml in 10 mM buffers
(losses in purity by SE-HPLC at +40 ± 2° C.)

| Formulation | Slopes (% degr./week) | | | Loss in purity (%) after 1 month | | |
|---|---|---|---|---|---|---|
| | PHO* | CITR.* | ACE* | PHO* | CITR.* | ACE* |
| 5 mg/ml at pH = 4.0 | / | −0.07 | −0.10 | / | −0.3% | −0.4% |
| 5 mg/ml at pH = 5.0 | −0.33 | −0.24 | −0.32 | −1.3% | −0.9% | −1.3% |
| 5 mg/ml at pH = 6.0 | −0.17 | −0.10 | −0.17 | −0.7% | −0.4% | −0.7% |
| 5 mg/ml at pH = 7.0 | −0.40 | −0.15 | / | −1.6% | −0.6% | / |
| 5 mg/ml at pH = 8.0 | −8.45 | / | / | −33.8% | / | / |
| 50 mg/ml at pH = 4.0 | / | −0.68 | −1.56 | / | −2.7% | −6.2% |
| 50 mg/ml at pH = 5.0 | −1.79 | −0.95 | −1.79 | 7.2% | −3.8% | −7.2% |
| 50 mg/ml at pH = 6.0 | −0.65 | −0.50 | −0.70 | −2.6% | −2.0% | −2.8% |
| 50 mg/ml at pH = 7.0 | −0.86 | −0.78 | / | −3.4% | −3.1% | / |
| 50 mg/ml at pH = 8.0 | −10.88 | / | / | −43.5% | / | / |

*PHO = sodium phosphate buffer, CITR. = sodium citrate buffer, ACE = sodium acetate buffer As shown by the table above and the graphs a pH dependence is observed both at 5 mg/ml and 50 mg/ml: the minor loss of purity % was observed at pH 6.0 and 7.0 for both strengths. Also citrate and acetate buffer at pH 4.0 had a positive effect on the aggregate content while at pH 8.0 in phosphate buffer a fast degradation path was observed.

No oxidation by HI-HPLC or change in pH or appearance was observed after 1 month storage at +40±2° C.

Ionic Strength Effect

Figure 4:
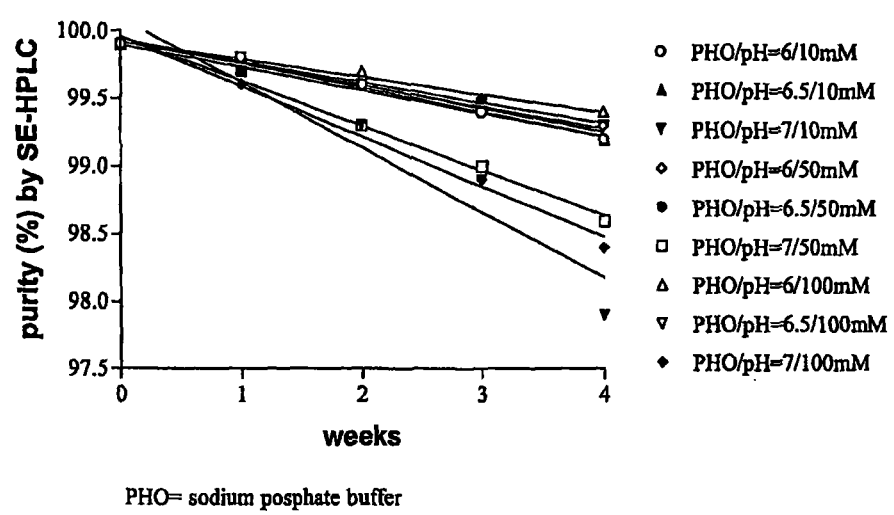
FIG. 4 shows linear regression lines for onercept formulated bulk at 5 mg/ml at different ionic strength (stability data at +40±2° C.).
Figure 5:
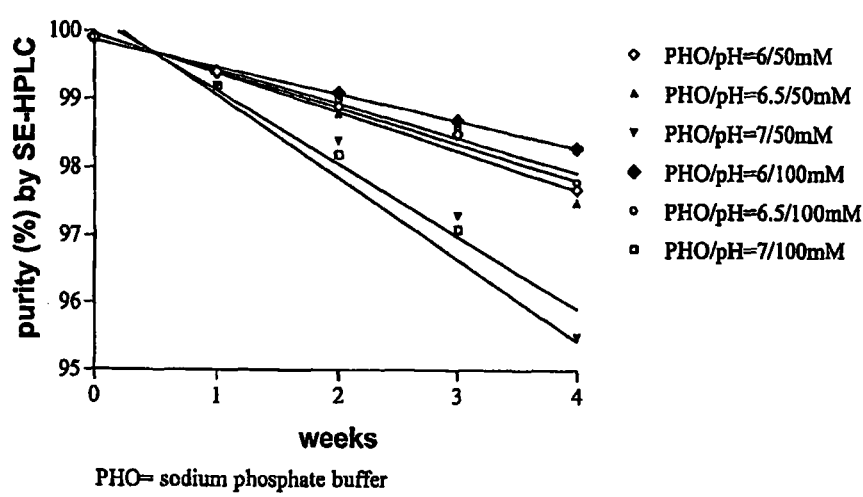
FIG. 5 shows linear regression lines for onercept formulated bulk at 50 mg/ml at different ionic strength (stability data at +40±2° C.).

In order to test the effect of various ionic strengths, solutions of onercept at 5 mg/ml and 50 mg/ml were prepared in phosphate buffer at three different molarities (10 mM, 50 mM and 100 mM) at pH 6.0, 6.5, and 7.0 each. The solutions (about 20 ml/batch) were filled into 3 ml glass vials (1 ml filling volume), capped, stoppered and stored at +5±3° C., +25±2° C. and +40±2° C. to be analysed weekly up to 1 month. Results were as shown by the Graphs of FIGS. 4 and 5 and by Table 2:

TABLE 2

Onercept formulated bulk at 5 mg/ml and 50 mg/ml at different ionic strengths
(losses in purity by SE-HPLC at +40 ± 2° C.)

| Formulation | Slopes (% degr./week) | | | Loss in purity (%) after 1 month | | |
|---|---|---|---|---|---|---|
| | pH 6.0 | pH 6.5 | pH 7.0 | pH 6.0 | pH 6.5 | pH 7.0 |
| 5 mg/ml in 10 mM phosphate buffer | −0.18 | −0.17 | −0.48 | −0.7% | −0.7% | −1.9% |
| 5 mg/ml in 50 mM phosphate buffer | −0.15 | −0.17 | −0.33 | −0.6% | −0.7% | −1.3% |
| 5 mg/ml in 100 mM phosphate buffer | −0.13 | −0.16 | −0.37 | −0.5% | −0.6% | −1.5% |
| 50 mg/ml in 50 mM phosphate buffer | −0.53 | −0.57 | −1.07 | −2.1% | −2.3% | −4.3% |
| 50 mg/ml in 100 mM phosphate buffer | −0.39 | −0.50 | −1.21 | −1.6% | −2.0% | −4.5% |

As shown by the graphs and the table above the extent of aggregation is not affected by the buffer concentration: pH 7.0 has a negative effect on purity % at each buffer strength while a minor loss in purity was observed both at pH 6.0 and 6.5. No oxidation by HI-HPLC nor change in pH or appearance was observed after 1 month storage at +40±2° C.

Other Excipients (Stabilizers) Effect

In order to test the effect of various excipients, solutions of onercept at 5 mg/ml and 50 mg/ml were prepared in phosphate buffer 40 mM at pH 6.0 and 6.5 and brought to isotonicity with sodium chloride, mannitol, glucose and saccharose. The solutions (about 20 ml/batch) were filled into 3 ml glass vials (1 ml filling volume), capped, stoppered and stored at +5±3° C., +25±2° C. and +40±2° C. to be analysed weekly up to 1 month.

Figure 6:
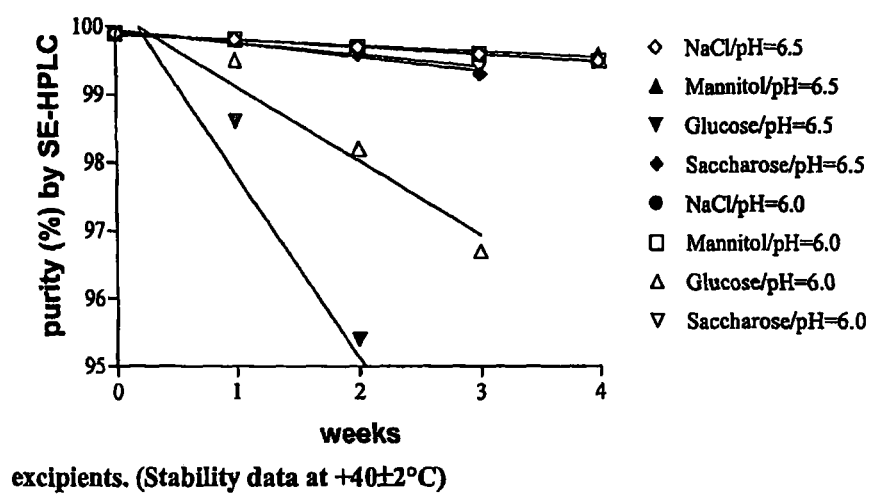
FIG. 6 shows linear regression lines for onercept formulated bulk at 5 mg/ml with excipients (stability data at +40±2° C.).
Figure 7:
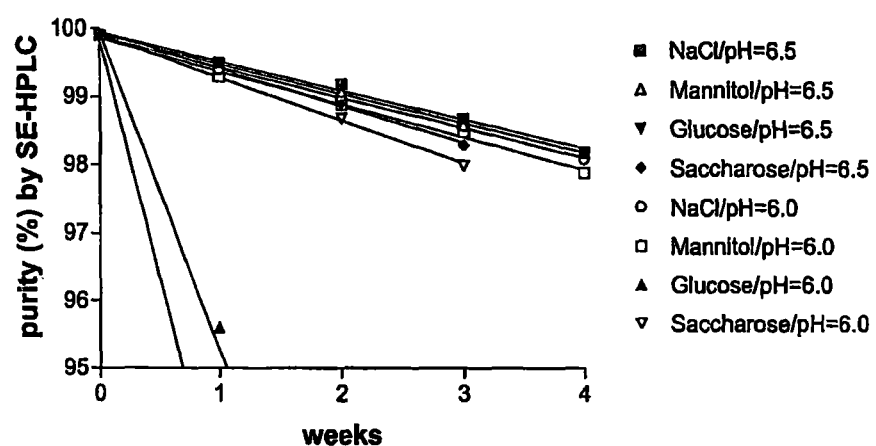
FIG. 7 shows linear regression lines for onercept formulated bulk at 50 mg/ml with excipients (stability data at +40±2° C.).

Results were as shown by the Graphs of FIGS. 6 and 7 and by Table 3:

TABLE 3

Onercept formulated bulk at 5 mg/ml and 50 mg/ml with excipients
(losses in purity by SE-HPLC at +40 ± 2° C.)

| Formulation | Slopes (% degr./week) | | Loss in purity (%) after 1 month | |
|---|---|---|---|---|
| | pH = 6.0 | pH = 6.5 | pH = 6.0 | pH = 6.5 |
| 5 mg/ml with sodium chloride | −0.10 | −0.10 | −0.4% | −0.4% |
| 5 mg/ml with mannitol | −0.10 | −0.08 | −0.4% | −0.3% |
| 5 mg/ml with saccharose | −0.17 | −0.20 | −0.7% | −0.8% |
| 5 mg/ml with glucose | −1.09 | −2.7 | −4.4% | −10.8 |
| 50 mg/ml with sodium chloride | −0.44 | −0.42 | −1.8% | −1.7% |
| 50 mg/ml with mannitol | −0.48 | −0.43 | −1.9% | −1.7% |
| 50 mg/ml with saccharose | −0.63 | −0.54 | −2.5% | −2.2% |
| 50 mg/ml with glucose | −4.66 | −6.97 | −18.6% | −27.9% |

As shown by the Graphs and the Table above sodium chloride and mannitol had the same behaviour as isotonicity agents. Consequently, sodium chloride was selected being already present in the drug substance solution. Further, no pH shift occurred after one month storage at +40±2° C. while a modified pattern on the chromatographic profile was observed by HI-HPLC for the onercept formulations containing glucose and saccharose as stabilizers.

From all these results, the surprising conclusion comes that the most stable liquid formulations are those excipients, which are normally used as stabilizers. Therefore the most stable formulations are those, which contain only an appropriate buffer to dilute the active substance and an isotonicity agent.

In these conditions, the pH range applicable for good stability results is 6.0 to 7, preferably from 6 to 6.5. Isotonicity can be obtained by the addition of adequate amounts of sodium chloride or mannitol, preferably sodium chloride.

Further, analogous experiments have confirmed substantially the same results for strengths of TBP-1 up to 170 mg/ml, as well as for TBP-2.

EXAMPLES OF PHARMACEUTICAL PRODUCTION

Materials
r-h TBP-1 drug substance; Sodium chloride (Merck); di-Sodium hydrogen phosphate dihydrate (Merck); Sodium dihydrogen phosphate monohydrate (Merck); ortho-Phosphoric acid 85% (Merck); WFI.

Container/Closure
The primary container is a glass syringe with a stainless steel needle and rubber plunger. It is composed of:

SYRINGE

Description:
SCF 1.0 mL long W7974 grey (Becton Dickinson)
Material, Composition:
syringe: borosilicate glass type I
needle: steel
lubricant: DC360, silicone oil-dimethicone
needle shield: elastomer

PLUNGER STOPPER

Description:
HYPAK SCF plunger stopper; BSCF 1.0 mLL 4023/50 grey (Becton Dickinson)
Material, Composition:
elastomer: bromobutyl, inert mineral, unconventional curing system
lubricant: DC360, silicone oil-dimethicone
Example of Preparation of r-h TBP-1 Solutions in 0.1 M Sodium Phosphate Buffer, pH=6.5; Sodium Chloride 0.025 M
A) Solution of r-h TBP-1 at 14.3 mg/mL
For the preparation of a batch of 1 L of finished product, the following quantities are used:

| | |
|---|---|
| r-h TBP-1 | 14.3 g |
| Sodium Chloride | 1.46 g |
| di-Sodium phosphate dihydrate | 10.5 g |
| Sodium dihydrogen phosphate monohydrate | 5.68 g |

B) Solution of r-h TBP-1 at 71.4 mg/mL
For the preparation of a batch of 1 L of finished product, the following quantities are used:

| | |
|---|---|
| r-h TBP-1 | 71.4 g |
| Sodium Chloride | 1.46 g |
| di-Sodium phosphate dihydrate | 10.5 g |
| Sodium dihydrogen phosphate monohydrate | 5.68 g |

C) Solution of r-h TBP-1 at 142.9 mg/mL
For the preparation of a batch of 1 L of finished product, the following quantities are used:

| | |
|---|---|
| r-h TBP-1 | 142.9 g |
| Sodium Chloride | 1.46 g |
| di-Sodium phosphate dihydrate | 10.5 g |
| Sodium dihydrogen phosphate monohydrate | 5.68 g |

Method of Preparation
The liquid drug substance containing r-h TBP-1 is lyophilized and the resulting powder is collected to be titred.
The required quantities of sodium chloride, disodium phosphate dihydrate and sodium dihydrogen phosphate monohydrate are dissolved in approximately 800 g of WFI. Their amounts are calculated taking into account the contribution of salts coming from the lyophilized drug substance.
The pH is checked and adjusted to the value of 6.5±0.2 with diluted (1:10) ortho-phosphoric acid 85%.
The required amount of lyophilized drug substance is added very slowly under stirring and WFI is added to reach the final weight (calculated considering the final density of the solution). The pH is checked and adjusted to pH 6.5±0.2 with diluted ortho-phosphoric acid, at various steps during compounding.
The r-h TBP-1 solution is first pre-filtered through a 0.45 μm membrane filter followed by a sterile filtration on a 0.22 μm membrane filter (DURAPORE) under 1.0 tam nitrogen pressure (the solution at 14.3 mg/mL is not pre-filtered). The sterile solution is collected into a glass flask.

The invention claimed is:
1. A stable, pharmaceutically acceptable, aqueous formulation, the formulation comprising a recombinant extracellular fragment of human TNF-binging protein-2, an isotonicity agent selected from the group consisting of sodium chloride and mannitol, and a buffer selected from the group consisting of a phosphate buffer, acetate buffer, and citrate buffer.
2. The formulation according to claim 1, wherein the buffer is a phosphate buffer.
3. The formulation according to claim 1, wherein the buffer is an acetate buffer.
4. The formulation according to claim 1, in which the buffer is a citrate buffer.
5. The formulation according to claim 2, in which the buffer keeps the pH from 5 to 7.
6. The formulation according to claim 3, in which the buffer keeps the pH from 4 to 6.
7. The formulation according to claim 4, in which the buffer keeps the pH from 4 to 7.
8. The formulation according to claim 1, wherein the concentration of the TNF-binding protein is from 5 to 170 mg/ml.
9. The formulation according to claim 1, wherein the concentration of the buffer is from 5 to 150 mM.
10. The formulation according to claim 1, wherein the concentration of the isotonicity agent is from 5 to 50 mM.

11. The formulation according to claim 1, further comprising a preservative.

12. The formulation according to claim 11, wherein the preservative is selected from the group consisting of phenol, benzyl alcohol, meta-cresol, methyl paraben, propyl paraben, benzalconium chloride, and benzethonium chloride.

13. A process for the preparation of a stable, pharmaceutically acceptable, aqueous formulation according to claim 1, comprising diluting the recombinant, extracellular fragment of human TNF-binding protein-2 with an isotonicity agent selected from the group consisting of sodium chloride and mannitol, and a buffer selected from the group consisting of a phosphate buffer, acetate buffer, and citrate buffer TNF-binding protein with a solution of excipients.

14. A presentation form of the stable, pharmaceutically acceptable, aqueous pharmaceutical formulation according to claim 1, comprising a container appropriate for storage prior to use wherein the liquid formulation is hermetically sealed under sterile conditions.

* * * * *